(12) United States Patent
Ballerini et al.

(10) Patent No.: US 11,974,790 B2
(45) Date of Patent: May 7, 2024

(54) OSTEOSYNTHESIS DEVICE WITH PLATE PROVIDED WITH A THREADED HOLE FOR RECEIVING A LOCKED FASTENING SCREW

(71) Applicant: NEWCLIP INTERNATIONAL, Luxembourg (LU)

(72) Inventors: Julien Ballerini, Nantes (FR); Grégoire Larche, Cholet (FR); Jean-Pierre Podgorski, Sevremoine (FR)

(73) Assignee: NEWCLIP INTERNATIONAL, Luxembourg (LU)

( * ) Notice: Subject to any disclaimer, the term of this patent is extended or adjusted under 35 U.S.C. 154(b) by 453 days.

(21) Appl. No.: 17/431,089

(22) PCT Filed: Feb. 13, 2020

(86) PCT No.: PCT/EP2020/053791
§ 371 (c)(1),
(2) Date: Aug. 13, 2021

(87) PCT Pub. No.: WO2020/165360
PCT Pub. Date: Aug. 20, 2020

(65) Prior Publication Data
US 2022/0133371 A1    May 5, 2022

(30) Foreign Application Priority Data
Feb. 14, 2019 (FR) ...................................... 1901476

(51) Int. Cl.
| *A61B 17/80* | (2006.01) |
|---|---|
| *A61B 17/58* | (2006.01) |
| *A61B 17/70* | (2006.01) |
| *A61B 17/17* | (2006.01) |

(52) U.S. Cl.
CPC ...... *A61B 17/8057* (2013.01); *A61B 17/1728* (2013.01); *A61B 17/58* (2013.01);
(Continued)

(58) Field of Classification Search
CPC ............ A61B 17/8057; A61B 17/8014; A61B 17/8052; A61B 17/8061; A61B 17/1728;
(Continued)

(56) References Cited

U.S. PATENT DOCUMENTS 8,574,268 B2    11/2013    Chan et al.
10,905,476 B2 *  2/2021    Lopez ................ A61B 17/8061
(Continued)

FOREIGN PATENT DOCUMENTS

| DE | 10 2015 102629 | 10/2016 |
|---|---|---|
| FR | 2928259 | 9/2009 |

OTHER PUBLICATIONS

International Search Report for PCT/EP2020/053791 dated Jun. 16, 2020, 6 pages.
(Continued)

*Primary Examiner* — Marcela I. Shirsat
(74) *Attorney, Agent, or Firm* — NIXON & VANDERHYE

(57) ABSTRACT

In an osteosynthesis device with a plate and a screw for fixing the plate on a bone, the head of the screw includes a thread for its locking with the internal thread in its receiving hole. The internal surface of the plate hole includes a first frustoconical section that extends at an angle 30-60° with respect to the hole central axis, and a second frustoconical section that extends between the first frustoconical section and the plate lower face, at an angle 8-12° with respect to the hole central axis. The internal surface of the hole also includes at least three upper undercuts, and at least three lower undercuts, which upper and lower undercuts allow a degree of freedom in angulation of the screw, and also preserve a portion of hole internal thread on all the generatrices of the hole internal surface located in planes parallel to the central axis.

20 Claims, 4 Drawing Sheets

(52) U.S. Cl.
CPC ....... *A61B 17/7058* (2013.01); *A61B 17/7059* (2013.01); *A61B 17/8014* (2013.01); *A61B 17/8052* (2013.01); *A61B 17/8061* (2013.01); *A61B 17/808* (2013.01)

(58) Field of Classification Search
CPC . A61B 17/58; A61B 17/7058; A61B 17/7059; A61B 17/808; A61B 17/84; A61B 17/8605
USPC .... 606/291, 60, 280, 70–71, 281–290, 86 R, 606/87, 86 B, 900–901
See application file for complete search history.

(56) References Cited

U.S. PATENT DOCUMENTS

| | | | | |
|---|---|---|---|---|
| 11,026,727 | B2* | 6/2021 | Bosshard | A61B 17/86 |
| 2008/0021477 | A1* | 1/2008 | Strnad | A61B 17/8047 606/287 |
| 2008/0140130 | A1* | 6/2008 | Chan | A61B 17/8605 606/301 |
| 2010/0312286 | A1* | 12/2010 | Dell'Oca | A61B 17/8057 606/291 |
| 2011/0015682 | A1 | 1/2011 | Lewis et al. | |
| 2011/0264149 | A1* | 10/2011 | Pappalardo | A61B 17/8019 606/86 R |
| 2012/0265253 | A1* | 10/2012 | Conley | A61B 17/808 606/286 |
| 2015/0374420 | A1 | 12/2015 | Hashmi et al. | |
| 2018/0064477 | A1 | 3/2018 | Lopez et al. | |
| 2018/0064479 | A1 | 3/2018 | Lopez et al. | |

OTHER PUBLICATIONS

Written Opinion of the ISA for PCT/EP2020/053791 dated Jun. 16, 2020, 6 pages.

* cited by examiner

OSTEOSYNTHESIS DEVICE WITH PLATE PROVIDED WITH A THREADED HOLE FOR RECEIVING A LOCKED FASTENING SCREW

CROSS-REFERENCE TO RELATED APPLICATIONS

This application is the U.S. national phase of International Application No. PCT/EP2020/053791 filed Feb. 13, 2020 which designated the U.S. and claims priority to French Application No. 1901476 filed Feb. 14, 2019, the entire contents of each of which are hereby incorporated by reference.

BACKGROUND OF THE INVENTION

Field of the Invention

The present invention generally relates to the plate and screw osteosynthesis devices that are used by surgeons to reduce a bone fracture. It more particularly relates to an osteosynthesis device provided with plate having a threaded hole for receiving a locked fixation screw.

Description of the Related Art

In the field concerned, document FR-2 928 259 describes a device, consisted of a plate associated with a set of screws, proposed to surgeons to reduce a bone fracture.

The osteosynthesis plate has a lower face intended to come into contact with the bone, and an opposite upper face. Its thickness is a few millimeters; and it is passed through by a plurality of holes, at least some of which receive screws for the fixation thereof pressed against the receiving bone material.

These holes may have a circular section (cross-section transverse to their axis), with a portion of periphery in the form of a truncated cone, against which the contour of the associated screw head comes into contact.

When the fixation screws are not locked to the plate, if the receiving bone material is not of good quality, there is a risk that these screws withdraw from the bone and the plate, and thereby a risk of loss of reduction, resulting in poor clinical outcome.

In such a case, it is therefore interesting to obtain a locking of the fixation screw to the osteosynthesis plate, this locking being obtained by a thread formed on the contour of the screw head, cooperating with a complementary internal thread formed on the periphery of the receiving hole.

In this context, document U.S. Pat. No. 8,574,268 proposes making a plurality of undercuts (or cutouts) regularly distributed over the whole height of the plate hole perimeter, in such a way as to define columns provided with threaded portions separated from each other. Such a feature gives the surgeon a possibility to adjust the inclination of the screw axis with respect to the axis of its receiving hole.

However, this type of device does not provide an optimum stability of the screw locked to the plate, in particular in the case where the screw is placed in the axis of the associated hole.

SUMMARY OF THE INVENTION

In order to remedy the above-mentioned drawback of the state of the art, the present invention provides a plate and screw osteosynthesis device for fixing said plate to a bone, which osteosynthesis device comprises:

an osteosynthesis plate comprising an upper face, a lower face intended to come into contact with the bone, and a plate hole extending through said plate, from said upper face to said lower face, which plate hole has an internal surface of generally frustoconical shape centered on a central axis and converging from said upper face to said lower face, which hole internal surface comprises a hole internal thread, and a screw comprising a screw head and a screw body, which screw body possibly comprises a thread for the fixation of said screw into the bone, and which screw head has a peripheral surface provided with a thread intended to cooperate with said hole internal thread for the locking of said screw to said osteosynthesis plate, this osteosynthesis device being characterized in that said internal surface of said plate hole comprises:

a first frustoconical section that extends from said plate upper face, or close to said plate upper face, at an angle between 30 and 60° with respect to said central axis, which first frustoconical section comprises a first frustoconical section upper portion, a second frustoconical section that extends between said first frustoconical section and said lower face, at an angle between 5 and 15° with respect to said central axis, which second frustoconical section comprises a second frustoconical section lower portion, which hole internal surface includes:

at least three upper undercuts, provided over at least part of height of said first frustoconical section from the upper portion of the latter, which at least three upper undercuts are regularly spaced apart around the periphery of said plate hole at a pitch P, and at least three lower undercuts, provided over at least part of height of said second frustoconical section and that extend to the lower portion of the latter, which at least three lower undercuts are in the same number as said at least three upper undercuts and are offset by half the pitch P with respect to these latter, which upper undercuts and lower undercuts extend at least over the depth of said hole internal thread and are arranged in such a way as to allow a degree of freedom in angulation of said screw housed in said plate hole, and which upper undercuts and lower undercuts are also arranged in such a way as to preserve a portion of hole internal thread on all the generatrices of the hole internal surface which are located in planes parallel to said central axis.

Such a combination of features allows for angulation of the screw axis with respect to the plate hole axis, while keeping a good stability of the locking between the screw and the plate. Moreover, it allows an optimized stress distribution and a good mechanical stability, in particular when locking the screw in the axis of its receiving hole.

Other non-limiting and advantageous features of the osteosynthesis device according to the invention, taken individually or according to all the technically possible combinations, are the following:

at least some of said upper and lower undercuts are in the form of a portion of a sphere;
at least some of said upper and lower undercuts are in the form of a portion of a cylinder;
the internal surface of the plate hole comprises four upper undercuts and four lower undercuts;

the hole internal thread is of the double-thread type, consisted of two threads offset by 180°;

the second frustoconical section of the internal surface of the plate hole extends in the continuation of the first frustoconical section;

the upper undercuts are provided over the whole height of the first frustoconical section and over part of height of the second frustoconical section;

the lower undercuts are provided over the whole or almost the whole height of said second frustoconical section;

an upper counterbore is provided between the upper face of the osteosynthesis plate and the upper portion of the first frustoconical section of the internal surface of the plate hole, and a lower chamfer is provided between the lower face of the osteosynthesis plate and the lower portion of the second frustoconical section of the internal surface of the plate hole.

Of course, the different features, alternatives and embodiments of the invention can be associated with each other according to various combinations, insofar as they are not mutually incompatible or exclusive.

BRIEF DESCRIPTION OF THE DRAWINGS

Moreover, various other features of the invention will be apparent from the appended description made with reference to the drawings that illustrate non-limitative embodiments of the invention, and wherein.

DESCRIPTION OF THE PREFERRED EMBODIMENTS

Figure 1:
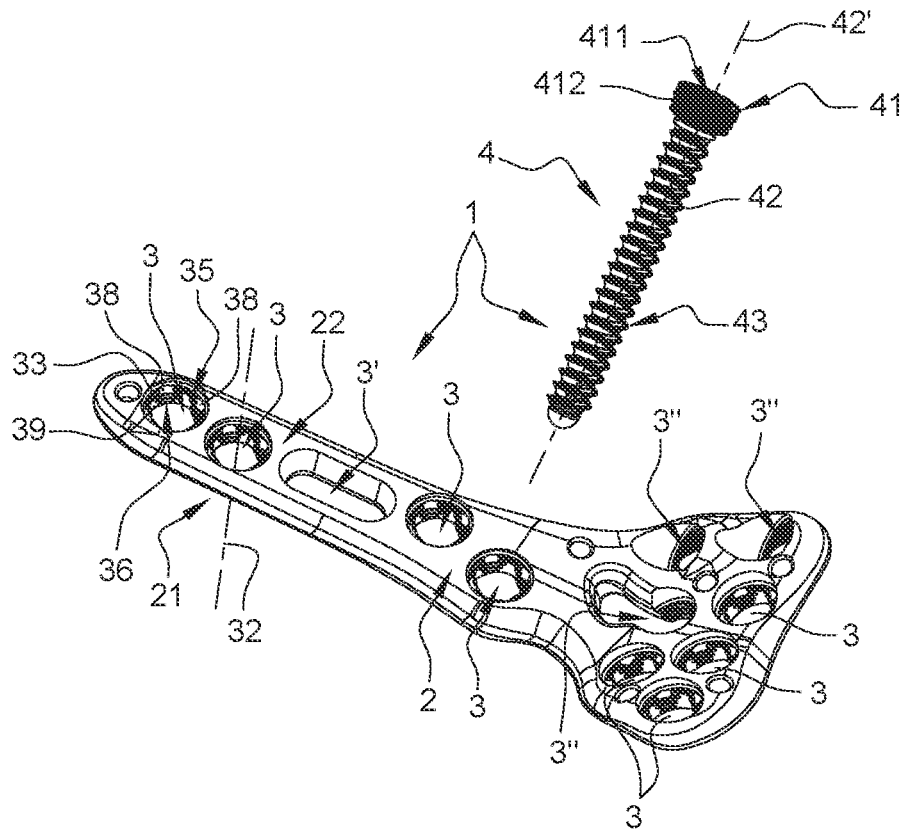
FIG. 1 is a perspective view of an osteosynthesis device according to the invention, comprising an osteosynthesis plate and one of its fixation screws, said fixation screw being shown spaced apart from the plate, not engaged into one of the fixing holes.
Figure 2:
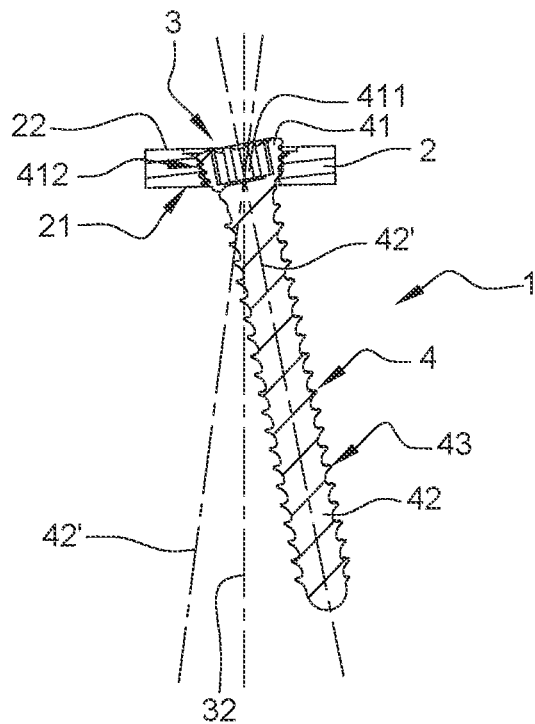
FIG. 2 is a partial cross-sectional view of the osteosynthesis plate shown in FIG. 1, with a fixation screw locked into one of the circular fixing holes.
Figure 3:
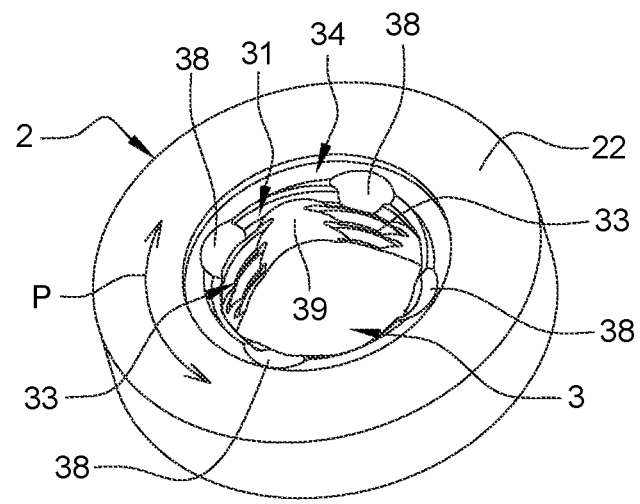
FIG. 3 is a partial perspective view of the osteosynthesis plate shown in FIG. 1, detailing one of its fixing holes, viewed from the side of the upper face of the plate.
Figure 5:
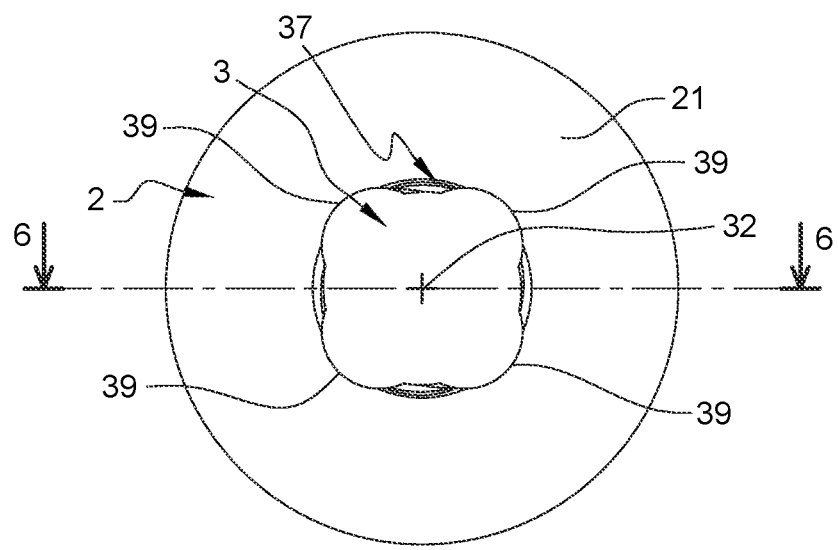
FIG. 5 shows the fixing hole of FIG. 3, viewed from below, i.e. from the side of the lower face of the osteosynthesis plate.
Figure 6:
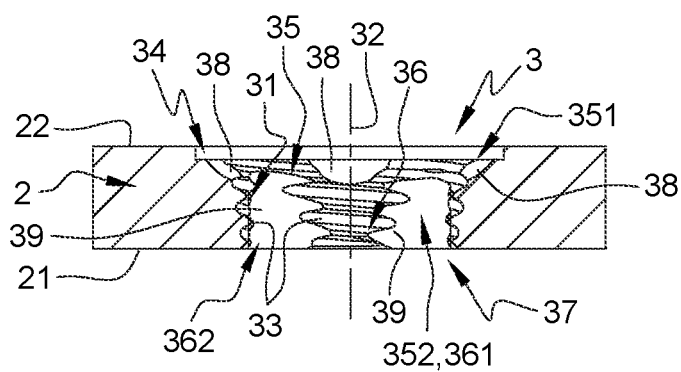
FIG. 6 is a cross-sectional view along the section plane 6-6 of FIG. 5.
Figure 4:
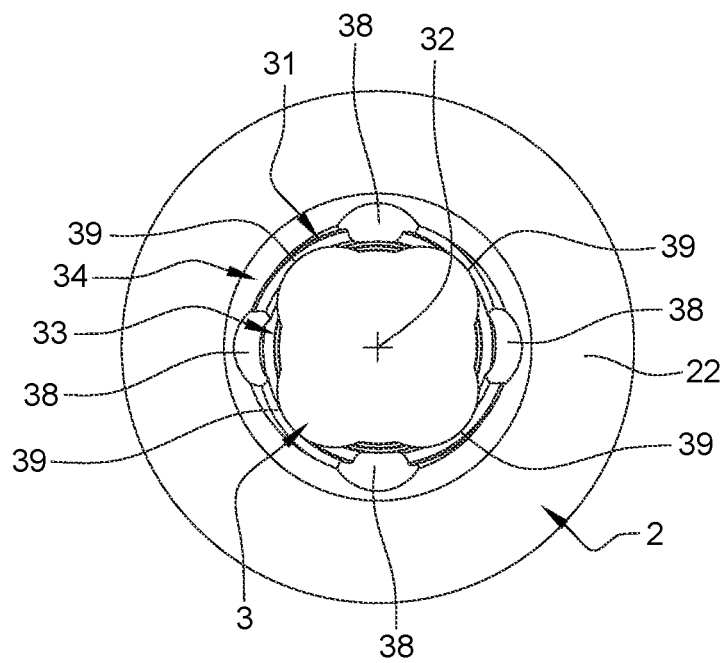
FIG. 4 shows the fixing hole of FIG. 3, viewed from above, i.e. from the side of the upper face of the osteosynthesis plate.

The osteosynthesis device 1 illustrated in FIGS. 1 and 2 is adapted for the reduction of a bone fracture.

This osteosynthesis device 1 comprises an osteosynthesis plate 2, whose thickness is a few millimeters, delimited by a lower face 21 intended to come into contact with the receiving bone material and by an opposite upper face 22.

This osteosynthesis plate 2 is provided with a plurality of holes 3, 3', 3" that go through its thickness, between its lower face 21 and its upper face 22, and that are intended for the passage of fixation screws, for the fixation thereof to the receiving bone material.

Here, a plurality of these holes 3 have a generally circular shape (more precisely a section transverse to their axis that is circular) and their internal surface is structured in a particular manner, detailed hereinafter, to allow a poly-axial locking of a fixation screw 4 intended to be implanted into the receiving bone material. One of these fixation screws 4 is shown in FIG. 1, shown spaced apart from the osteosynthesis plate 2. FIG. 2 shows this fixation screw 4 in an active position, locked in its receiving hole 3 on the osteosynthesis plate 2.

The osteosynthesis plate 2 illustrated in FIG. 1 also includes:

an oblong hole 3' that allows the adjustable positioning in translation of a fixation screw, and three threaded holes 3", each for the receiving and the mono-axial locking of a fixation screw.

The fixation screw 4 illustrated in FIGS. 1 and 2 is consisted of—a head 41, at least a part of the contour of which is intended to come into contact with a part of the periphery of one of the circular holes 3, and—a screw body 42, of longitudinal axis 42', provided with a thread 43 for its anchoring into the receiving bone material. An indentation 411 made in the screw head 41 allows the screw 4 to be rotated by means of a suitable tool, for its implantation into the receiving bone material.

It will be noted that, in an alternative embodiment, the screw body 42 can be devoid of thread.

The contour of the screw head 41 has a generally truncated shape and includes a head thread 412, here of the double-thread type consisted of two threads offset by 180°.

The structure of the internal surface of the hole 3 is detailed in FIGS. 3 to 6.

This hole 3 of the osteosynthesis plate 2 has an internal surface 31 of generally truncated shape centered on a central axis 32 and that converges from the upper face 22 to the lower face 21.

The hole internal surface 31 comprises a hole internal thread 33, adapted to cooperate with the head thread 412 of the fixation screw 4 to allow the locking of this screw 4 to the osteosynthesis plate 2; and it is also structured in such a way as to allow an angulation of the fixation screw 4 with respect to the central axis 32 of the hole 3, in such a way as to give the surgeon a possibility to adjust the position of this fixation screw 4.

This angulation possibility is illustrated in FIG. 2 in which is shown the axis 42' of the screw body 42 angularly offset with respect to the hole central axis 32. This possible angulation may be of the order of 10° about the hole central axis 32 (i.e. 20° as a whole).

For that purpose, the hole internal surface 31 comprises, successively, from the upper face 22 to the lower face 21:

an upper counterbore 34, a first frustoconical section 35 that extends at an angle A (visible in FIG. 7) between 30 and 60° with respect to the central axis 32 (preferably, this angle A is between 40 and 50°), a second frustoconical section 36 that extends at an angle B (visible in FIG. 7) between 5 and 15° with respect to the central axis 32 (preferably, this angle B is between 8 and 12°, and still preferably between 9 and 11°), and an outlet lower chamfer 37.

The upper counterbore 34 extends between the upper face 22 of the osteosynthesis plate 2 and the upper portion 351 of the first frustoconical section 35.

Preferably, the first frustoconical section extends over a height between quarter and half the height of the second frustoconical section.

The second frustoconical section 36 extends in the continuation of the first frustoconical section 35; thus, the lower portion 352 of the first frustoconical section 35 is juxtaposed to the upper portion 361 of the second frustoconical section 36.

The lower chamfer 37 extends between the lower portion 362 of the second frustoconical section 36 and the lower face 21 of the osteosynthesis plate 2.

On the other hand, according to the invention, the hole internal surface 31 also comprises a plurality of undercuts (or cuttings or cutouts) adapted to optimize the desired possibilities of inclination of the fixation screw 4, i.e.: at least three upper undercuts 38, regularly distributed over the periphery of the hole 3 at a pitch P, and at least three lower undercuts 39, also regularly distributed over the periphery of the hole 3 at a pitch P, these lower undercuts 39 being in the same number as the upper undercuts 38 and being offset by half the pitch P with respect to these latter.

The upper undercuts 38 are advantageously between three and eight in number, preferably four in number, as shown in the appended figures (the pitch is hence of 90°). They are arranged over at least part of the height of the first frustoconical section 35 from the upper portion 351 of the latter, and advantageously over the whole height of this first frustoconical section 35 and over part of the height of the second frustoconical section 36.

The lower undercuts 39 are advantageously between three and eight in number, preferably four in number, as shown in the appended figures (the pitch is hence of 90°). They are arranged over at least part of the height (and preferably over the whole or almost the whole height) of the second frustoconical section, to the lower portion 362 of the latter.

The upper undercuts 38 and the lower undercuts 39 extend at least over the depth of the hole internal thread 33 and are arranged in such a way as to allow a degree of freedom in angulation of said fixation screw 4 housed in the associated plate hole 3. Moreover, they are also arranged in such a way as to preserve a portion of hole internal thread 33 on all the generatrices of the hole internal surface 31 which are located in planes parallel to said central axis 32.

Such a combination of features makes it possible to obtain a good mechanical stability of the locking between the fixation screw and the osteosynthesis plate (due to the presence of at least one internal thread portion over any axial cross-section of the periphery of the hole 3), while benefiting from the searched poly-axial nature of the fixation screw.

The slops of the first and second frustoconical sections 35, 36, as well as the number, shape and depth of the upper 38 and lower 39 undercuts, are adapted as a function of the desired compromise between the locking mechanic stability quality and the possible degree of angularity.

Figure 7:
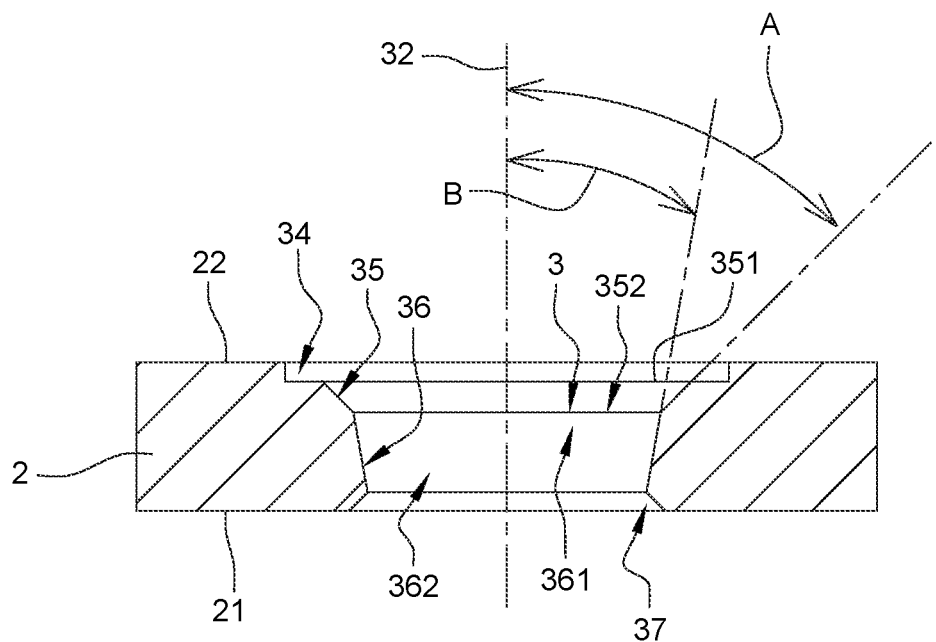
FIG. 7 is a cross-sectional view of the preform of the fixing hole of FIGS. 3 to 6, before the making of the internal thread and of the upper and lower undercuts.

Such holes 3 are first obtained by making a circular hole preform as shown in FIG. 7, with the upper counterbore 34, the first frustoconical section 35, the second frustoconical section 36 and the outlet lower chamfer 37.

Figure 8:
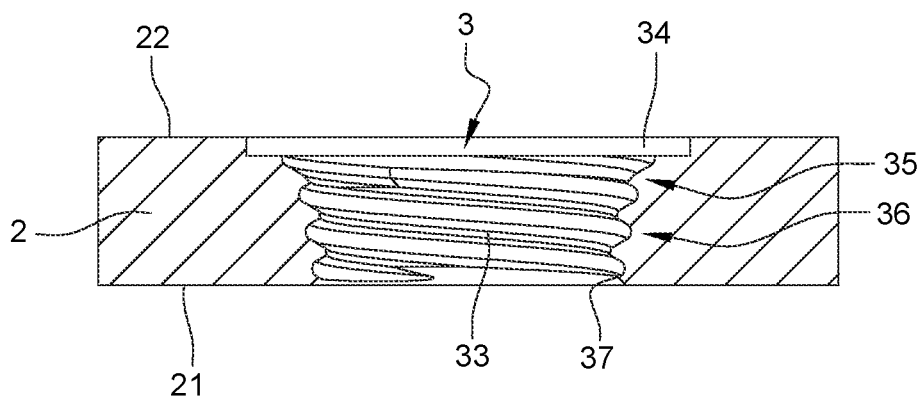
FIG. 8 shows the hole preform of FIG. 7, after the making of the internal thread thereof and before the making of the upper and lower undercuts.

Then, as illustrated in FIG. 8, the hole internal thread 33 is made over the whole internal surface 31 of the hole 3. This internal thread is preferably of the double-thread type, consisted of two threads offset by 180°.

This internal thread 33 follows the preform shape, i.e. it follows the two slops of the hole.

Finally, the lower 39 and upper 38 undercuts are for example but not necessarily made in this order.

Figure 9:
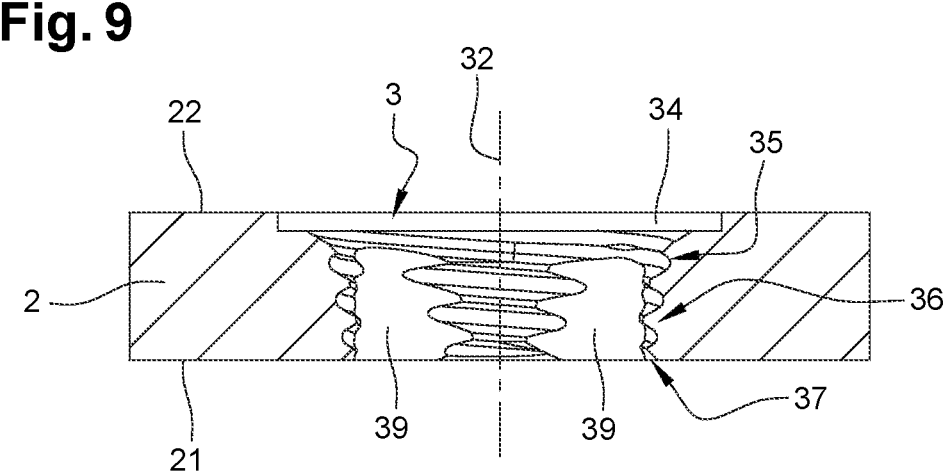
FIG. 9 shows the hole preform of FIG. 8, after the making of the lower undercuts and before the making of the upper undercuts.

FIG. 9 shows the plate hole 3 during its preparation, after the making of the lower undercuts 39, and before the making of the upper undercuts 38.

These lower undercuts 39 may be in the form of a portion of a cylinder having an axis that is inclined or not with respect to the axis 32 of the hole 3.

The upper undercuts 38 are then made to obtain the final hole structure as shown in FIGS. 3 to 6.

These upper undercuts 38 can be in the form of a portion of sphere, or a portion of cylinder.

The invention claimed is:

1. A plate and screw osteosynthesis device for fixing said plate on a bone, which osteosynthesis device comprises:
    an osteosynthesis plate comprising an upper face, a lower face intended to come into contact with the bone, and a plate hole extending through said plate, from said upper face to said lower face,
    which plate hole has an internal surface of generally frustoconical shape centered on a central axis and converging from said upper face to said lower face,
    which hole internal surface comprises a hole internal thread, and
    a screw comprising a screw head and a screw body, which screw head has a peripheral surface provided with a thread intended to cooperate with said hole internal thread for the locking of said screw to said osteosynthesis plate,
    wherein said internal surface of said plate hole comprises:
        a first frustoconical section that extends from said plate upper face, or close to said plate upper face, at an angle between 30 and 60° with respect to said central axis, which first frustoconical section comprises a first frustoconical section upper portion,
        a second frustoconical section that extends between said first frustoconical section and said lower plate face, at an angle between 5 and 15° with respect to said central axis, which second frustoconical section comprises a second frustoconical section lower portion,
    which hole internal surface includes:
        at least three upper undercuts, provided over at least part of height of said first frustoconical section from the upper portion of the first frustoconical section, which at least three upper undercuts are regularly spaced apart around the periphery of said plate hole at a pitch P, and
        at least three lower undercuts, provided over at least part of height of said second frustoconical section and that extend to the lower portion of the second frustoconical section,
    which at least three lower undercuts are in the same number as said at least three upper undercuts and are offset by half the pitch P with respect to said at least three upper undercuts, which upper undercuts and lower undercuts extend at least over the depth of said hole internal thread and are arranged in such a way as to allow a degree of freedom in angulation of said screw housed in said plate hole,
    and which upper undercuts and lower undercuts are also arranged in such a way as to preserve a portion of hole internal thread on all the generatrices of the hole internal surface which are located in planes parallel to said central axis.

2. The osteosynthesis device according to claim 1, wherein at least certain of said upper and lower undercuts are in the form of a portion of a sphere.

3. The osteosynthesis device according to claim 2, wherein at least certain of said upper and lower undercuts are in the form of a portion of a cylinder.

4. The osteosynthesis device according to claim 2, further comprising four upper undercuts and four lower undercuts.

5. The osteosynthesis device according to claim 2, wherein said hole internal thread is of the double-thread type consisted of two threads offset by 180°.

6. The osteosynthesis device according to claim 2, wherein said second truncated section extends in the continuation of said first truncated section.

7. The osteosynthesis device according to claim 2, wherein said lower undercuts are arranged over the whole or almost the whole height of said second truncated section.

8. The osteosynthesis device according to claim 1, wherein at least certain of said upper and lower undercuts are in the form of a portion of a cylinder.

9. The osteosynthesis device according to claim 8, further comprising four upper undercuts and four lower undercuts.

10. The osteosynthesis device according to claim 8, wherein said hole internal thread is of the double-thread type consisted of two threads offset by 180°.

11. The osteosynthesis device according to claim 8, wherein said second truncated section extends in the continuation of said first truncated section.

12. The osteosynthesis device according to claim 1, further comprising four upper undercuts and four lower undercuts.

13. The osteosynthesis device according to claim 12, wherein said hole internal thread is of the double-thread type consisted of two threads offset by 180°.

14. The osteosynthesis device according to claim 12, wherein said second truncated section extends in the continuation of said first truncated section.

15. The osteosynthesis device according to claim 1, wherein said hole internal thread is of the double-thread type consisted of two threads offset by 180°.

16. The osteosynthesis device according to claim 15, wherein said second truncated section extends in the continuation of said first truncated section.

17. The osteosynthesis device according to claim 1, wherein said second truncated section extends in the continuation of said first truncated section.

18. The osteosynthesis device according to claim 17, wherein said upper undercuts are arranged over the whole height of said first frustoconical section and over part of the height of said second frustoconical section.

19. The osteosynthesis device according to claim 1, wherein said lower undercuts are arranged over the whole or almost the whole height of said second truncated section.

20. The osteosynthesis device according to claim 1, further comprising:
an upper counterbore between the upper face of said osteosynthesis plate and said upper portion of the first frustoconical section, and
a lower chamfer between the lower face of said osteosynthesis plate and said lower portion of the second frustoconical section.

* * * * *